(12) United States Patent
Parikh et al.

(10) Patent No.: US 11,406,584 B2
(45) Date of Patent: Aug. 9, 2022

(54) HAIR COSMETIC COMPOSITIONS CONTAINING GUMS, FATTY ALCOHOL, AND ESTERS

(71) Applicant: L'OREAL, Paris (FR)

(72) Inventors: Dhara Parikh, New Brunswick, NJ (US); Vanessa Comeron-Decarlo, Roselle Park, NJ (US); Emma Naiberk, Maplewood, NJ (US); Aziza Khader Suleiman, Paterson, NJ (US)

(73) Assignee: L'OREAL, Paris (FR)

( * ) Notice: Subject to any disclaimer, the term of this patent is extended or adjusted under 35 U.S.C. 154(b) by 89 days.

(21) Appl. No.: 16/584,238

(22) Filed: Sep. 26, 2019

(65) Prior Publication Data
US 2021/0093543 A1   Apr. 1, 2021

(51) Int. Cl.
| | |
|---|---|
| A61Q 5/12 | (2006.01) |
| A61Q 5/06 | (2006.01) |
| A61K 8/92 | (2006.01) |
| A61K 31/736 | (2006.01) |
| A61K 8/73 | (2006.01) |
| A61K 8/04 | (2006.01) |
| A61K 8/06 | (2006.01) |
| A61K 8/37 | (2006.01) |
| A61K 8/60 | (2006.01) |

(52) U.S. Cl.
CPC .............. *A61K 8/737* (2013.01); *A61K 8/042* (2013.01); *A61K 8/06* (2013.01); *A61K 8/375* (2013.01); *A61K 8/602* (2013.01); *A61K 8/922* (2013.01); *A61Q 5/06* (2013.01); *A61Q 5/12* (2013.01)

(58) Field of Classification Search
None
See application file for complete search history.

(56) References Cited

U.S. PATENT DOCUMENTS

2013/0315846 A1* 11/2013 Collier .................. A61K 8/894
424/59

FOREIGN PATENT DOCUMENTS

| WO | 02096369 A2 | 12/2002 |
| WO | 2018218000 A1 | 11/2018 |

OTHER PUBLICATIONS

Bis-Diglyceryl Polyacyladipate-2. https://cosmeticsinfo.org/ingredient/bis-diglyceryl-polyacyladipate-2-0. Published: Feb. 25, 2016.*
International Search Report and Written Opinion dated Mar. 12, 2021 for corresponding PCT Application No. PCT/US2020/052365.

* cited by examiner

*Primary Examiner* — David J Blanchard
*Assistant Examiner* — Lori K Mattison
(74) *Attorney, Agent, or Firm* — Polsinelli PC

(57) ABSTRACT

The instant disclosure relates to hair cosmetic compositions that include a unique combination of components that function to impart desirable cosmetic properties to hair, in particular, curly hair. The hair cosmetic compositions typically include a nonionic guar gum; a gum selected from xanthan gum and *sclerotium* gum, a fatty alcohol, esters selected from glyceryl ester and a second ester, plant- or vegetable-based fatty component comprising coconut oil and shea butter, and water.

20 Claims, 2 Drawing Sheets

HAIR COSMETIC COMPOSITIONS CONTAINING GUMS, FATTY ALCOHOL, AND ESTERS

FIELD OF THE DISCLOSURE

The instant disclosure relates to hair cosmetic compositions that are particularly useful for improving the quality of hair, in particular, curly hair, and which can impart beneficial properties such as styling/shaping, curl elongation, curl definition, frizz control, retention of shape/curl, curl pick up, discipline as well as hydration, moisture, and smoothness. Also disclosed are methods for using the hair cosmetic compositions.

BACKGROUND

Many consumers desire to use cosmetic and care compositions that enhance the appearance of keratinous substrates such as hair, e.g., by changing the color, style, and/or shape of the hair, and/or by imparting various cosmetic properties to hair, such as shine and conditioning. Many of the known compositions and processes for enhancing the appearance of hair involve chemical treatments to the hair.

The process of changing the color of hair, for example, can involve depositing an artificial color onto the hair which provides a different shade or color to the hair, and/or lifting the color of the hair, such as lightening the color of dark hair to lighter shades, which m requires the use of oxidizing agents.

Additionally, there are many techniques and compositions for styling or altering the shape of hair. For example, hair care products referred to as "hair relaxers" or "hair straighteners" can relax or straighten curly or kinky hair, including wavy hair. Straightening or relaxing the curls of very curly hair may increase the manageability and ease of styling of such hair. Compositions for permanent waving the hair will impart a curl or a wave to otherwise straight hair. Different types of compositions can be applied onto hair in order to change its shape and make it more manageable, such as alkaline and acidic compositions. Hair relaxers, straighteners, perms, and/or waves may either be applied in a hair salon by a professional or in the home by the individual consumer.

While dyeing or color lifting compositions can effectively alter the color of hair, and relaxing, straightening, perming, and waving compositions can effectively alter the shape of the hair, these chemical treatments can damage the hair fibers and/or irritate the scalp. Thus, in order to reduce or avoid damage to hair, as well as to improve the cosmetic performance of the compositions, different types of hair styling products have been developed by manufacturers that are aimed to help consumers achieve a desired look, including one or more of fuller hair, thicker hair, sleek and straight hair, frizz-free hair, and defined curls. These products are typically provided in forms that are applied after the shampooing and conditioning processes are completed.

In one example, styling products are available that provide protection against external factors such as protection from moisture to minimize or reduce frizziness. To achieve this benefit, a water-resistant film or coating may be applied to the hair using film-forming polymers. Depending on the chemical make-up of the film-forming polymers. Product formulations that include these polymers can tend to be viscous, i.e. as the concentration of the polymer increases its viscosity builds up rapidly. Translated to styling applications, as the solvent evaporates, the polymer solution becomes thicker on the hair surface, leaving a sticky or tacky film residue on the hair. This often leaves hair with a stiff and/or sticky feeling and/or too much "crunch" (i.e. the films become hard and brittle and therefore have a crunchy feel or sound when manipulated), which is undesirable to many consumers.

Increasingly, consumers also seek hair products that have a natural look and feel, a light-weight feel, while imparting good styling benefits to hair. Further, consumers seek products that offer multiple benefits, for example, combining frizz reduction and style hold with softening, elongation or lengthening effects while still providing good curl definition. Moreover, consumers desire hair products that can protect hair from extreme environmental conditions such as high humidity which causes the hair to become very frizzy, unmanageable, and lose its shape and style.

One important functional element of such products is their ability to style the hair without weighing it down. Many consumers seek hair products which have excellent style memory, cosmeticity, and shine without heavily coating the hair strands, and thereby weighing the hair down. The resulting feel and texture of the hair after the application are important elements of such commodities. While different technologies and products exist in the market for hair styling products, there is still a need for improvement in these areas as well as the need to provide caring benefits that are not typically found in a styling product.

In the multicultural beauty market, consumers with curly hair often have curls that shrink or coil up. This shrinking causes the hair to appear much shorter than the actual hair length. Longer hair is often associated with healthier hair. This leads to a consumer desire for products that give more visual length to the hair in order for it to look healthier. Traditionally, the products on the market that give this elongating benefit are extremely heavy (ex. hair oils or heavy creams) and leave the hair feeling greasy or dirty. They can also cause heavy product buildup, flaking, and scalp irritation. This requires more frequent washing, which the consumer does not desire. Other options that give elongating effects are styling gels, but these gels flake on the hair, leave the hair too stiff and crunchy, and lack moisture.

Thus, the object of this invention is related to a composition and method of treating hair utilizing hair compositions which will deliver both caring and styling/shaping benefits to hair such as frizz control, discipline, control/hold, softness, smoothness, shine, natural feel, and hydration, but will not result in any product build up or leave the hair feeling heavily coated or weighed down, stiff, or brittle.

The object of the invention is also to deliver all other styling benefits that curly haired consumers desire on a daily basis: curl definition, moisture, conditioning, hold, frizz control, curl/shape retention, curl pick up, moisture to curls, and not leaving the curls feeling greasy or stiff, and in particular, curl elongation or stretching or lengthening. The composition from such an invention can be applied on wet or damp hair using a "wash and go" or "twist out" method. "Wash and go" involves applying the product, section by section, to wet or damp hair and letting it air dry. The "twist out" method involves manipulating the curl pattern in order to provide elongation while maintaining other styling benefits. It can be done by applying the product on wet hair and twisting small sections of the hair and letting it air dry.

The object of the invention is also to provide these attributes that will last even when hair is exposed to high humidity conditions. The invention is particularly useful for treating and providing the described properties to curly hair (of varying degrees of curl) and to wavy hair.

SUMMARY OF THE DISCLOSURE

It has surprisingly been found that compositions and methods of treating hair according to the present invention impart styling/shaping, curl elongation or stretching or lengthening, curl definition, curl retention, curl pick up, frizz control, volume control, control/hold, discipline, hydration, moisture, and smoothness and other cosmetic benefits to the hair, while still providing a light weight feel and a clean feel (non-greasy, non-oily) to the hair.

One aspect of the invention pertains to a hair cosmetic composition comprising:
(a) a first gum selected from nonionic guar gums;
(b) a second gum selected from xanthan gum, *sclerotium* gum, and a mixture thereof;
(c) at least one fatty alcohol in an amount of about 1.5 to about 8 wt %;
(d) at least one glyceryl ester in an amount of about 0.5 to about 5 wt % and selected from glyceryl stearate, bis-diglyceryl polyacyladipate, and a mixture thereof;
(e) at least one ester that is not a glyceryl ester in an amount of about 0.5 to about 3 wt %;
(f) a plant- or vegetable-based fatty component comprising coconut oil and shea butter; and
(g) water;
all weights being based on the total weight of the hair cosmetic composition.

Another aspect of the invention pertains to methods of treating hair, such as styling or shaping hair, including improving/altering/maintaining the style or shape of hair. In some embodiments, the method comprises applying any of the compositions described herein to hair. In one or more embodiments, the composition is applied to hair, including curly hair, as part of a hair styling/shaping or caring routine. In some embodiments, the composition is applied after treating the hair with a shampoo and/or conditioner and/or a masque (mask).

BRIEF DESCRIPTION OF THE DRAWING

Implementation of the present technology will now be described, by way of example only, with reference to the attached figures, wherein.

Figure 1:
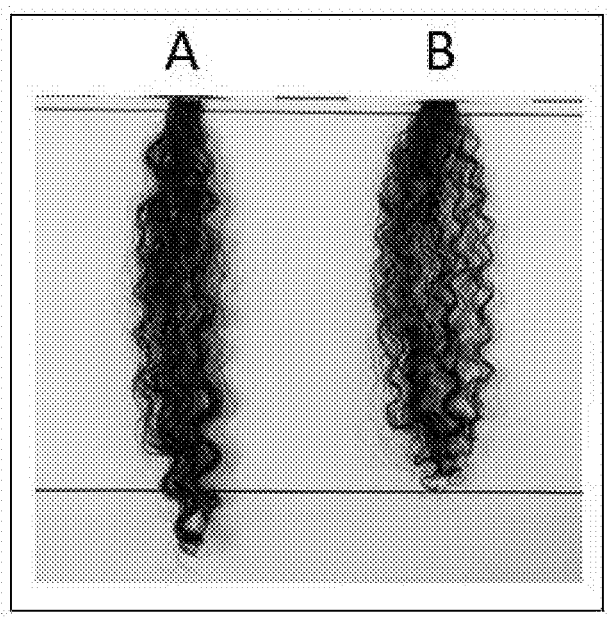
FIG. 1 includes pictures of hair swatches in which the left side was treated with the composition of the invention and the right side was treated with a comparative formula.

It should be understood that the various aspects are not limited to the arrangements and instrumentality shown in the drawings.

DETAILED DESCRIPTION OF THE DISCLOSURE

The term "hair cosmetic composition" encompasses many types of compositions for application to the hair, for example, hair lotions, hair emulsion creams, hair gel creams, hair conditioners, hair masques (masks), etc., which can be used either as leave-on or rinse-off treatments or products. A hair cosmetic composition according to the invention is characterized by its ability to provide a cosmetic (such as styling/shaping and caring) benefit to the hair. Non-limiting examples of benefits that can be imparted by the compositions of the present invention to hair include frizz control, curl definition, curl retention, curl pick-up, styling/shaping, discipline, volume control, hold/control, manageability, smoothness, softness, suppleness, hydration (does not feel dry) and natural feel. At the same time, even when the compositions of the present disclosure contain fatty compounds such as fatty alcohols, esters, and plant- or vegetable-based oils, surprisingly, a light weight feel and a clean feel (non-greasy, non-oily) are imparted to the hair.

The hair cosmetic compositions of the instant disclosure typically include:
(a) a first gum selected from nonionic guar gums;
(b) a second gum selected from xanthan gum, *sclerotium* gum, and a mixture thereof;
(c) at least one fatty alcohol in an amount of about 1.5 to about 8 wt %;
(d) at least one glyceryl ester in an amount of about 0.5 to about 5 wt % and selected from glyceryl stearate, bis-diglyceryl polyacyladipate, and a mixture thereof;
(e) at least one ester that is not a glyceryl ester in an amount of about 0.5 to about 3 wt %;
(f) a plant- or vegetable-based fatty component comprising coconut of and shea butter; and
(g) water;
all weights being based on the total weight of the hair cosmetic composition.

In an embodiment, the first gum of the present invention, selected from nonionic gums, includes hydroxypropyl guar.

In an embodiment, the first gum of the present invention, selected from nonionic gums, is present in an amount of about 0.1 to about 3 wt. %, preferably about 0.4 to about 2.5 wt. %, more preferably about 0.5 to about 2 wt. %, based on the total weight of the hair cosmetic composition.

In an embodiment, the second gum of the present invention is xanthan gum.

In an embodiment, the second gum of the present invention is *sclerotium* gum.

In an embodiment, the second gum is present in an amount of about 0.01 to about 3 wt. %, preferably about 0.05 to about 2 wt. %, more preferably about 0.1 to about 1 wt. %, based on the total weight of the hair cosmetic composition.

In an embodiment, the at least one fatty alcohol of the present invention is selected from cetyl alcohol, stearyl alcohol, cetearyl alcohol (combination of cetyl alcohol and stearyl alcohol), behenyl alcohol, lauryl alcohol (1-dodecanol); myristic or myristyl alcohol (1-tetradecanol), arachidyl alcohol (1-eicosanol), lignoceryl alcohol (1-tetracosanol); ceryl alcohol (1-hexacosanol); montanyl alcohol (1-octacosanol); myricylic alcohol (1-triacontanol), decyl alcohol, undecyl alcohol, and a mixture thereof.

In an embodiment, the at least one fatty alcohol of the present invention is selected from cetyl alcohol, stearyl alcohol, and cetearyl alcohol (combination of cetyl alcohol and stearyl alcohol).

In an embodiment, the at least one fatty alcohol is present in an amount of about 1.5% to about 6%, or from about 2% to about 6%, or from about 2% to about 5%, or from about 2 to about 4 wt. %, based on the total weight of the hair cosmetic composition.

In an embodiment, the at least one glyceryl ester of the present invention is glyceryl stearate.

In an embodiment, the at least one glyceryl ester of the present invention is bis-diglyceryl polyacyladipate.

In an embodiment, the at least one glyceryl ester is present in an amount of about 0.6 to about 4.5 wt. %, or preferably about 0.8 to about 4 wt. %, or more preferably, about 1 to about 3 wt. %, based on the total weight of the hair cosmetic composition.

In an embodiment, the at least one least one ester that is not a glyceryl ester of the present invention is selected from isopropyl esters, cetyl esters, or mixtures thereof.

In an embodiment, the at least one least one ester that is not a glyceryl ester includes isopropyl esters selected from isopropyl myristate, isopropyl laurate, isopropyl oleate, isopropyl palmitate, isopropyl stearate, or mixtures thereof.

In an embodiment, the at least one least one ester that is not a glyceryl ester includes isopropyl myristate, isopropyl palmitate, or a mixture thereof.

In an embodiment, the at least one least one ester that is not a glyceryl ester is isopropyl myristate.

In an embodiment, the at least one least one ester that is not a glyceryl ester is isopropyl palmitate.

In an embodiment, the at least one ester that is not a glyceryl ester is present in an amount of about 0.1 to about 5 wt. %, or about 0.5 to about 3.5 wt. %, or preferably about 0.6 to about 3 wt. %, or more preferably about 0.6 to about 2.5 wt. %, based on the total weight of the hair cosmetic composition.

In an embodiment, the plant- or vegetable-based fatty component is present in an amount of about 0.01 to about 5 wt. %, or about 0.5 to about 4.5 wt %, preferably, about 0.7 to about 4 wt. %, or more preferably, about 0.9 to about 3.5 wt. %, based on the total weight of the hair cosmetic composition.

In an embodiment, the plant- or vegetable-based fatty component further comprises castor seed oil.

In an embodiment, the hair cosmetic composition of the present invention includes at least one alkylpolyglucoside present in an amount of about 0.1 to about 8 wt. %, or about 0.15 to about 3 wt. %, or preferably, 0.2 to about 2 wt. %, or more preferably, 0.3% to about 1 wt. %, based on the total weight of the hair cosmetic composition.

In an embodiment, the alkylpolyglucoside is selected from Arachidyl Glucoside, C12-20 Alkyl Glucoside, Caprylyl/Capryl Glucoside, Cetearyl Glucoside, Coco-Glucoside, Lauryl Glucoside, Decyl Glucoside, or mixtures thereof.

In an embodiment, the alkylpolyglucoside is selected from Cetearyl Glucoside, Coco-Glucoside, Lauryl Glucoside, Decyl Glucoside, or mixtures thereof.

In an embodiment, the alkylpolyglucoside is Cetearyl Glucoside.

In an embodiment, the hair cosmetic composition of the present invention is in the form of a gel cream and comprises:
(a) a first gum selected from hydroxypropyl guar;
(b) a second gum selected from xanthan gum;
(c) at least one fatty alcohol present in an amount of about 1.5 to about 8 wt. % and selected from cetyl alcohol, stearyl alcohol, cetearyl alcohol (combination of cetyl alcohol and stearyl alcohol), behenyl alcohol, lauryl alcohol (1-dodecanol); myristic or myristyl alcohol (1-tetradecanol), arachidyl alcohol (1-eicosanol), lignoceryl alcohol (1-tetracosanol); ceryl alcohol (1-hexacosanol); montanyl alcohol (1-octacosanol); myricylic alcohol (1-triacontanol), decyl alcohol, undecyl alcohol, and a mixture thereof, and preferably, selected from cetyl alcohol, stearyl alcohol, and cetearyl alcohol (combination of cetyl alcohol and stearyl alcohol), and more preferably, selected from cetearyl alcohol;
(d) at least one glyceryl ester in an amount of about 0.6 to about 4.5 wt % and selected from glyceryl stearate;
(e) at least one ester that is not a glyceryl ester in an amount of about 0.1 to about 5 wt. %, and selected from isopropyl myristate; and
(f) a plant- or vegetable-based fatty component comprising coconut oil and shea butter, and optionally, castor seed oil; and
(g) water;
all weights being based on the total weight of the hair cosmetic composition.

In an embodiment, the hair cosmetic composition of the present invention is in the form of a gel cream and comprises:
(a) a first gum selected from hydroxypropyl guar;
(b) a second gum selected from xanthan gum;
(c) at least one fatty alcohol present in an amount of about 1.5 to about 8 wt. % and selected from cetyl alcohol, stearyl alcohol, cetearyl alcohol (combination of cetyl alcohol and stearyl alcohol), behenyl alcohol, lauryl alcohol (1-dodecanol); myristic or myristyl alcohol (1-tetradecanol), arachidyl alcohol (1-eicosanol), lignoceryl alcohol (1-tetracosanol); ceryl alcohol (1-hexacosanol); montanyl alcohol (1-octacosanol); myricylic alcohol (1-triacontanol), decyl alcohol, undecyl alcohol, and a mixture thereof, and preferably, selected from cetyl alcohol, stearyl alcohol, and cetearyl alcohol (combination of cetyl alcohol and stearyl alcohol), and more preferably, selected from cetearyl alcohol;
(d) at least one glyceryl ester in an amount of about 0.6 to about 4.5 wt % and selected from glyceryl stearate;
(e) at least one ester that is not a glyceryl ester in an amount of about 0.1 to about 5 wt. %, and selected from isopropyl myristate; and
(f) a plant- or vegetable-based fatty component comprising coconut oil, shea butter, and castor seed oil; and
(g) water;
all weights being based on the total weight of the hair cosmetic composition.

In an embodiment, the hair cosmetic composition of the present invention is in the form of an emulsion cream and comprises:
(a) a first gum selected from hydroxypropyl guar;
(b) a second gum selected from *sclerotium* gum;
(c) at least one fatty alcohol present in an amount of about 1.5 to about 8 wt. % and selected from cetyl alcohol, stearyl alcohol, cetearyl alcohol (combination of cetyl alcohol and stearyl alcohol), behenyl alcohol, lauryl alcohol (1-dodecanol); myristic or myristyl alcohol (1-tetradecanol), arachidyl alcohol (1-eicosanol), lignoceryl alcohol (1-tetracosanol); ceryl alcohol (1-hexacosanol); montanyl alcohol (1-octacosanol); myricylic alcohol (1-triacontanol), decyl alcohol, undecyl alcohol, and a mixture thereof, and preferably, selected from cetyl alcohol, stearyl alcohol, and cetearyl alcohol (combination of cetyl alcohol and stearyl alcohol), and more preferably, selected from cetearyl alcohol;
(d) at least one glyceryl ester in an amount of about 0.6 to about 4.5 wt % and selected from;
(e) at least one ester that is not a glyceryl ester in an amount of about 0.1 to about 5 wt. %, and selected from bis-diglyceryl polyacyladipate; and
(f) a plant- or vegetable-based fatty component comprising coconut oil and shea butter;
(g) water; and
(h) at least one alkylpolyglucoside selected from Arachidyl Glucoside, C12-20 Alkyl Glucoside, Caprylyl/Capryl Glucoside, Cetearyl Glucoside, Coco-Glucoside, Lauryl Glucoside, Decyl Glucoside, or mixtures thereof, and preferably, selected from Cetearyl Glucoside, Coco-Glucoside, Lauryl Glucoside, Decyl Glucoside, or mixtures thereof, and more preferably selected from cetearyl glucoside;

all weights being based on the total weight of the hair cosmetic composition.

The present invention is also directed to a method of treating hair, as styling or shaping hair, including improving/altering/maintaining the style or shape of hair. The method comprises applying onto hair, a hair cosmetic composition comprising:

(a) a first gum selected from nonionic guar gums, including hydroxypropyl guar;

(b) a second gum selected from xanthan gum, *sclerotium* gum, and a mixture thereof;

(c) at least one fatty alcohol in an amount of about 1.5 to about 8 wt. % and selected from cetyl alcohol, stearyl alcohol, cetearyl alcohol (combination of cetyl alcohol and stearyl alcohol), behenyl alcohol, lauryl alcohol (1-dodecanol); myristic or myristyl alcohol (1-tetradecanol), arachidyl alcohol (1-eicosanol), lignoceryl alcohol (1-tetracosanol); ceryl alcohol (1-hexacosanol); montanyl alcohol (1-octacosanol); myricylic alcohol (1-triacontanol), decyl alcohol, undecyl alcohol, and a mixture thereof, and preferably, selected from cetyl alcohol, stearyl alcohol, and cetearyl alcohol (combination of cetyl alcohol and stearyl alcohol), and more preferably, selected from cetearyl alcohol;

(d) at least one glyceryl ester in an amount of about 0.6 to about 4.5 wt % and selected from;

(e) at least one ester that is not a glyceryl ester in an amount of about 0.1 to about 5 wt. %, and selected from glyceryl stearate, bis-diglyceryl polyacyladipate, or a mixture thereof; and (f) a plant- or vegetable-based fatty component comprising coconut oil and shea butter and optionally, castor seed oil;

(g) water; and (h) optionally, at least one alkylpolyglucoside selected from Arachidyl Glucoside, C12-20 Alkyl Glucoside, Caprylyl/Capryl Glucoside, Cetearyl Glucoside, Coco-Glucoside, Lauryl Glucoside, Decyl Glucoside, or mixtures thereof, and preferably, selected from Cetearyl Glucoside, Coco-Glucoside, Lauryl Glucoside, Decyl Glucoside, or mixtures thereof, and more preferably selected from cetearyl glucoside;

all weights being based on the total weight of the hair cosmetic composition;

In an embodiment, the above-described compositions are silicone-free.

In an embodiment, the above-described compositions are mineral oil-free.

In an embodiment, the method of the present invention comprises applying the cosmetic composition of the present disclosure onto hair, wherein the method imparts to hair one or more of:

shaping or styling benefits;
curl elongation (or curl stretching or curl lengthening);
curl definition;
curl retention;
long-lasting curl definition;
humidity-resistant curl definition;
frizz control;
styling/shaping hold;
smoothness;
softness;
natural feel;
hydration;
light-weight feel;
shine; or
crunch.

The above compositions, which feature a unique combinations of ingredients, advantageously provide frizz control, volume control, curl elongation or stretching or lengthening, curl definition, curl retention, curl pick-up, discipline, hold/control, styling/shaping, long lasting or humidity-resistant styling and curl care benefits together with natural feel, light-weight feel, non-oily or non-greasy feel, softness, and smoothness.

The hair cosmetic compositions described herein may be in any suitable physical form. Suitable forms include, but are not limited to low to moderate viscosity liquids, lotions, milks, gel creams, emulsion creams, pastes, clays, conditioners, masks, and the like.

The hair cosmetic compositions may be packaged in a variety of different containers, such as, for example, a ready-to-use container. Non-limiting examples of useful packaging include tubes, jars, caps, unit dose packages, and bottles, including squeezable tubes and bottles and spray bottles.

First Gum (Nonionic Guar Gums)

The first gum of the compositions of the present invention is selected from nonionic guar gums, including hydroxypropyl guar gum.

The total amount of the first gum in the composition, if present, may vary but is typically from about 0.1 to about 3 wt. %, based on the total weight of the composition. In some instances, the total amount of the first gum is from about 0.15 to about 3 wt. %, or about 0.2 to about 2.8 wt. %, or about 0.3 to about 2.6 wt. %, or about 0.35 to about 2.5 wt. %, or about 0.4 to about 2.4 wt. %, or about 0.45 to about 2.2 wt. %, or about 0.5 to about 2 wt. %, based on the total weight of the composition, including ranges and sub-ranges there between.

Thus, the first gum is present, by weight, based on the total weight of the composition, in an amount from about 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, to about 3 wt. %, including increments and ranges therein and there between.

Second Gum

The second gum of the compositions of the present invention is selected from xanthan gum, *sclerotium* gum, or a mixture thereof.

The total amount of the second gum in the composition, if present, may vary but is typically from about 0.01 to about 3 wt. %, based on the total weight of the composition. In some instances, the total amount of the second gum is from about 0.05 to about 3 wt. %, or about 0.05 to about 2.8 wt. %, or about 0.08 to about 2.5 wt. %, or about 0.1 to about 2 wt. %, or about 0.1 to about 1.5 wt. %, or about 0.1 to about 1 wt. %, based on the total weight of the composition, including ranges and sub-ranges there between.

Thus, the second gum is present, by weight, based on the total weight of the composition, in an amount from about 0.01, 0.02, 0.04, 0.05, 0.06, 0.08, 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, to about 3 wt. %, including increments and ranges therein and there between.

Fatty Alcohol

In accordance with the disclosure, compositions hereof include at least one fatty alcohol.

The term "fatty alcohol" means an alcohol comprising at least one hydroxyl group (OH), and comprising at least 8 carbon atoms, and which is neither oxyalkylenated (in particular neither oxyethylenated nor oxypropylenated) nor glycerolated. The fatty alcohols can be represented by: R—OH, wherein R denotes a saturated (alkyl) or unsaturated (alkenyl) group, linear or branched, optionally substituted with one or more hydroxyl groups, comprising from 8 to 40 carbon atoms, preferably 10 to 30 carbon atoms, more preferably 12 to 24 carbon atoms, and even more preferably 14 to 22 carbon atoms.

The fatty alcohol(s) may be liquid or solid. In some instances, it is preferable that the hair cosmetic compositions include at least one solid fatty alcohol. The solid fatty alcohols that can be used include those that are solid at ambient temperature and at atmospheric pressure (25° C., 780 mmHg), and are insoluble in water, that is to say they have a water solubility of less than 1% by weight, preferably less than 0.5% by weight, at 25° C., 1 atm.

The solid fatty alcohols may be represented by: R—OH, wherein R denotes a linear alkyl group, optionally substituted with one or more hydroxyl groups, comprising from 8 to 40 carbon atoms, preferably 10 to 30 carbon atoms, more preferably 12 to 24 carbon atoms, and even more preferably 14 to 22 carbon atoms.

In particular, it is possible to mention, alone or as a mixture: lauryl alcohol or lauryl alcohol (1-dodecanol); myristic or myristyl alcohol (1-tetradecanol); cetyl alcohol (1-hexadecanol); stearyl alcohol (1-octadecanol); arachidyl alcohol (1-eicosanol); behenyl alcohol (1-docosanol); lignoceryl alcohol (1-tetracosanol); ceryl alcohol (1-hexacosanol); montanyl alcohol (1-octacosanol); myricylic alcohol (1-triacontanol).

Preferably, the solid fatty alcohol is chosen from cetyl alcohol, stearyl alcohol, behenyl alcohol and mixtures thereof such as cetylstearyl or cetearyl alcohol.

The liquid fatty alcohols, in particular those containing C10-C34, preferably have branched carbon chains and/or have one or more, preferably 1 to 3 double bonds. They are preferably branched and/or unsaturated (C=C double bond), and contain from 12 to 40 carbon atoms.

The liquid fatty alcohols may be represented by: R—OH, wherein R denotes a C12-C24 branched alkyl group or an alkenyl group (comprising at least one C12-C24 double bond C=C), R being optionally substituted by a or more hydroxy groups. Preferably, the liquid fatty alcohol is a branched saturated alcohol. Preferably, R does not contain a hydroxyl group. These include oleic alcohol, linoleic alcohol, linolenic alcohol, isocetyl alcohol, isostearyl alcohol, 2-octyl-1-dodecanol, 2-butyloctanol, 2-hexyl-1-decanol, 2-decyl-1-tetradecanol, 2-tetradecyl-1-cetanol and mixtures thereof. Preferably, the liquid fatty alcohol is 2-octyl-1-dodecanol.

In some instances, the hair cosmetic compositions include one or more fatty alcohols selected from decyl alcohol, undecyl alcohol, dodecyl, myristyl, cetyl alcohol, stearyl alcohol, cetearyl alcohol, isostearyl alcohol, isocetyl alcohol, behenyl alcohol, linalool, oleyl alcohol, myricyl alcohol and a mixture thereof. In some instances, the hair cosmetic compositions preferably include cetearyl alcohol.

In accordance with the various embodiments, when present, the amount of each of the at least one fatty alcohol is from about 1.5% to about 8%, or from about 1.5% to about 6%, or from about 2% to about 6%, or from about 2% to about 5%, or from about 2 to about 4 wt. %, any suitable combination, sub-combination, range, or sub-range thereof by weight, based on the weight of the composition.

Thus, any one of the at least one fatty alcohol is present, by weight, based on the total weight of the composition, in an amount of from 1.5, 1.6, 1.7, 1.8, 1.9, 2, 2.1, 2.2, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5., 5.2, 5.3, 5.4, 5.5, 5.6, 5.7, 5.8, 5.9, 6, 6.2, 6.2, 6.3, 6.4, 6.5, 6.6, 6.7, 6.8, 6.9, 7, 7.1, 7.2, 7.3, 7.4, 7.5, 7.6, 7.7, 7.8, 7.9, to about 8 wt. %, including increments and ranges therein and there between.

Glyceryl Ester (Glycerol Esters)

The at least one glyceryl ester may be chosen from glyceryl stearate or bis-diglyceryl polyacyladipate-2 (sold under the trade mark SOFTISAN 649 by the company Cremer Oleo or under the trademark SP SUPERMOL B MBAL-SS-(RB) by the company Croda.

The total amount of the glyceryl ester(s) in the composition, if present, may vary but is typically from about 0.6 to about 4.5 wt. %, based on the total weight of the composition. In some instances, the total amount of glyceryl ester(s) is from about 0.6 to about 4.4 wt. %, or about 0.7 to about 4.2 wt. %, or about 0.8 to about 4 wt. %, or about 0.85 to about 3.8 wt. %, or about 0.9 to about 3.5 wt. %, or about 1 to about 3 wt. %, based on the total weight of the hair cosmetic composition, including ranges and sub-ranges there between.

Thus, any one of the at least one glyceryl ester is present, by weight, based on the total weight of the composition, in an amount from about 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, to about 4.5 wt. %, including increments and ranges therein and there between.

Ester that is not a Glyceryl Ester

The ester that is not a glyceryl ester in the compositions of the present invention is selected from isopropyl esters, cetyl esters, or a mixture thereof.

Suitable examples of isopropyl esters are isopropyl myristate, isopropyl laurate, isopropyl oleate, isopropyl palmitate, and isopropyl stearate.

In one embodiment, the ester that is not a glyceryl ester in the compositions of the present invention is selected from isopropyl myristate, isopropyl palmitate, or a mixture thereof.

In one embodiment, the ester that is not a glyceryl ester in the compositions of the present invention is isopropyl myristate.

The total amount of the at least one ester that is not a glyceryl ester in the composition, if present, may vary but is typically from about 0.1 to about 10 wt. %, based on the total weight of the composition. In some instances, the total amount of glyceryl ester(s) is from about 0.1 to about 8 wt. %, about 0.2 to about 8 wt. %, about 0.2 to about 7 wt. %, about 0.2 to about 6 wt. %, about 0.3 to about 5 wt. %, about 0.4 to about 5 wt. %, about 0.5 to about 4 wt. %, about 0.6 to about 3.5 wt. %, or about 0.6 to about 3 wt. %, based on the total weight of the composition including ranges and sub-ranges there between.

In other instances, the total amount of glyceryl ester(s) is from amount of about 0.1 to about 5 wt. %, or about 0.5 to about 3.5 wt. %, or preferably about 0.6 to about 3 wt. %, or more preferably about 0.6 to about 2.5 wt. %, based on the total weight of the composition including ranges and sub-ranges there between.

Thus, any one of the at least one ester that is not a glyceryl ester is present, by weight, based on the total weight of the composition, in an amount from about 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 6, 7, 8, 9, to about 10 wt. %, including increments and ranges therein and there between.

Plant- or Vegetable-Based Fatty Component

The plant- or vegetable-based fatty component of the compositions of the present invention comprise coconut oil and shea butter.

In one embodiment of the present invention, the plant- or vegetable-based fatty component consists of coconut oil and shea butter.

In one embodiment of the present invention, the plant- or vegetable-based fatty component further comprises Castor seed oil.

The total amount of the plant- or vegetable-based fatty component in the composition, if present, may vary but is typically from about 0.01 to about 10 wt. %, based on the total weight of the composition. In some instances, the total amount of plant- or vegetable-based fatty component is from about 0.01 to about 5 wt. %, or about 0.05 to about 5 wt. %, or about 0.05 to about 4.5 wt %, or about 0.08 to about 4.5 wt %, or about 0.1 to about 4.5 wt %, or about 0.5 to about 4.5 wt %, preferably, about 0.7 to about 4 wt. %, or more preferably, about 0.9 to about 3.5 wt. %, based on the total weight of the composition, including ranges and sub-ranges there between.

Thus, the plant- or vegetable-based fatty component is present, by weight, based on the total weight of the composition, in an amount from about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 6, 7, 8, 9, to about 10 wt. %, including increments and ranges therein and there between.

Oils Other than Coconut Oil or Shea Butter

Other plant- or vegetable-based oils may be included in the fatty component of the compositions of the present invention, as long as they do not result in a composition that is greasy or oily or heavy on the hair.

Thus, in an embodiment, the plant- or vegetable-based fatty component in the composition may further comprise another oil, such as for example, castor seed oil.

Water

The amount of water in the hair cosmetic compositions may be at least 50 wt. %, or from about 50 to about 95 wt. %, about 50 to about 90 wt. %, about 60 to about 90 wt. %, about 70 to about 88 wt. %, based on the weight of the composition.

Alkylpolyglucoside

In accordance with the disclosure, compositions hereof may include at least one alkylpolyglucoside. Useful alkylpolyglucosides include those having the following formula:

R1-O—(R2O)n—Z(x)     (I)

wherein:
R1 is an alkyl group having 8-18 carbon atoms;
R2 is an ethylene or propylene group;
Z is a saccharide group with 5-6 carbon atoms;
n is an integer ranging from 0 to 10; and
x is an integer ranging from 1 to 5.

Useful alkylpolyglucosides include selected from Arachidyl Glucoside, C12-20 Alkyl Glucoside, Caprylyl/Capryl Glucoside, Cetearyl Glucoside, Coco-Glucoside, Decyl Glucoside, sodium lauryl glucose carboxylate, or mixtures thereof. Typically, the alkyl polyglucoside compound is selected from the group consisting of cetearyl glucoside, lauryl glucoside, decyl glucoside, coco glucoside, or mixtures thereof. In some instances, cetearyl glucoside is particularly preferred.

In accordance with the various embodiments, the total amount of alkylpolyglucoside present in the compositions can range from about 0.1% to about 15%, or from about 0.2% to about 12%, or from about 0.3% to about 10%, or from about 0.3% to about 5% or any suitable combination, sub-combination, range, or sub-range thereof by weight, based on the weight of the composition. One of ordinary skill in the art, however, will appreciate that other ranges are within the scope of the invention. In accordance with some particular embodiments, at least one alkylpolyglucoside is present from about 0.1 to about 8 wt. %, or about 0.15 to about 3 wt. %, or preferably, 0.2 to about 2 wt. %, or more preferably, 0.3% to about 1 wt. %, based on the total weight of the composition, including ranges and sub-ranges there between.

Thus, any one of the at least one alkylpolyglucoside is present, by weight, based on the total weight of the composition, from about 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 6, 7, to about 8 wt. %, based on the total weight of the composition, including increments and ranges therein and there between.

Organic Solvents

The hair-treatment compositions may optionally include at least one organic solvent (non-silicone solvents).

Non-limiting examples of organic solvents include, for example, alcohols (for example, $C_{1-15}$, $C_{1-10}$, or $C_{1-6}$ alcohols), organic solvents, polyols (polyhydric alcohols and glycols (e.g., glycerin, butylene glycol, caprylyl glycol, etc.), and a mixture thereof.

Non-limiting examples of organic solvents include monoalcohols and polyols such as ethyl alcohol, isopropyl alcohol, propyl alcohol, benzyl alcohol, and phenylethyl alcohol, or glycerin or glycols or glycol ethers such as, for example, monomethyl, monoethyl and monobutyl ethers of ethylene glycol, propylene glycol or ethers thereof such as, for example, monomethyl ether of propylene glycol, butylene glycol, hexylene glycol, dipropylene glycol as well as alkyl ethers of diethylene glycol, for example monoethyl ether or monobutyl ether of diethylene glycol. Other suitable examples of organic solvents are ethylene glycol, propylene glycol, butylene glycol, hexylene glycol, propane diol, and glycerin. The organic solvents can be volatile or non-volatile compounds.

Further non-limiting examples of organic solvents include alkanediols such as 1,2,6-hexanetriol, trimethylolpropane, ethylene glycol, propylene glycol, diethylene glycol, triethylene glycol, tetraethylene glycol, pentaethylene glycol, dipropylene glycol, 2-butene-1,4-diol, 2-ethyl-1,3-hexanediol, 2-methyl-2,4-pentanediol, (caprylyl glycol), 1,2-hexanediol, 1,2-pentanediol, and 4-methyl-1,2-pentanediol; alkyl alcohols having 1 to 4 carbon atoms such as ethanol, methanol, butanol, propanol, and isopropanol; glycol ethers such as ethylene glycol monomethyl ether, ethylene glycol monoethyl ether, ethylene glycol monobutyl ether, ethylene glycol monomethyl ether acetate, diethylene glycol monomethyl ether, diethylene glycol monoethyl ether, diethylene glycol mono-n-propyl ether, ethylene glycol mono-iso-propyl ether, diethylene glycol mono-iso-propyl ether, ethylene glycol mono-n-butyl ether, ethylene glycol mono-t-butyl ether, diethylene glycol mono-t-butyl ether, 1-methyl-1-methoxybutanol, propylene glycol monomethyl ether, propylene glycol monoethyl ether, propylene glycol mono-t- butyl ether, propylene glycol mono-n-propyl ether, propylene glycol mono-iso-propyl ether, dipropylene glycol monomethyl ether, dipropylene glycol monoethyl ether, dipropylene glycol mono-n-propyl ether, and dipropylene glycol mono-iso-propyl ether; 2-pyrrolidone, N-methyl-2-pyrrolidone, 1,3-dimethyl-2-imidazolidinone, formamide, acetamide, dimethyl sulfoxide, sorbit, sorbitan, acetine, diacetine, triacetine, sulfolane, and a mixture thereof.

Polyhydric alcohols are useful. Examples of polyhydric alcohols include glycerin, ethylene glycol, diethylene glycol, triethylene glycol, propylene glycol, dipropylene glycol, tripropylene glycol, 1,3-butanediol, 2,3-butanediol, 1,4-butanediol, 3-methyl-1,3-butanediol, 1,5-pentanediol, tetraethylene glycol, 1,6-hexanediol, 2-methyl-2,4-pentanediol, polyethylene glycol, 1,2,4-butanetriol, 1,2,6-hexanetriol, and a mixture thereof. Polyol compounds may also be used. Non-limiting examples include the aliphatic diols, such as 2-ethyl-2-methyl-1,3-propanediol, 3,3-dimethyl-1,2-butanediol, 2,2-diethyl-1,3-propanediol, 2-methyl-2-propyl-1,3-propanediol, 2,4-dimethyl-2,4-pentanediol, 2,5-dimethyl-2,5-hexanediol, 5-hexene-1,2-diol, and 2-ethyl-1,3-hexanediol, and a mixture thereof.

The total amount organic solvent(s) in the hair cosmetic composition, if present, can vary but is typically about 0.1 to about 10 wt. %, based on the total weight of the hair cosmetic composition. In some cases, the total amount of water-soluble solvent(s) is about 0.1 to about 8 wt. %, about 0.1 to about 6 wt. %, about 0.1 to about 0.5 to about 10 wt. %, about 0.5 to about 8 wt. %, about 0.5 to about 6 wt. %, about 0.5 to about 5 wt. %, about 1 wt. %, about 2 wt. %, about 3 wt. %, or about 4 wt. %, including all ranges and subranges there between.

Other Components

In one or more embodiments, the hair cosmetic compositions described herein may contain one or more additional ingredients. Examples include, but are not limited to surfactants, emulsifiers, thickeners (such as polysaccharide-based or acrylate-based thickeners), fillers, sugars such as monosaccharides, aminosilicones, film formers, other polymers, fragrance, pH adjusters, and preservatives. Additional details regarding such additional ingredients follows below.

In an embodiment, the composition of the present disclosure may contain fillers such as calcium carbonate, talc, pigments, and mixtures thereof. The fillers may be used to provide more texture to the compositions.

In an embodiment, the composition of the present disclosure may contain monosaccharides or di-saccharides such as glucose, sucrose, xylose, ribose, and mixtures thereof. The mono- or di-saccharides can provide additional hold/control to hair.

In an embodiment, the compositions of the present disclosure are in the form of a leave-on cream product such as a styling/shaping product, leave-on product for curly hair (such as combing creams), anti-frizz hair product, or rinse-off or leave-on mask product.

In an embodiment, the compositions of the present disclosure are in the form of a rinse-off cream product such as a mask product.

In an embodiment, the compositions of the present disclosure are in the form of a leave-on cream product such as a styling/shaping product.

In an embodiment, the compositions of the present disclosure are in the form of a leave-on cream product such as a styling/shaping and conditioning product.

In an embodiment, the compositions of the present disclosure are in the form of a leave-on or a rinse-off styling conditioner.

In an embodiment, the compositions of the present disclosure are in the form of an emulsion such as an oil-in-water emulsion or a water-in-oil emulsion. In an embodiment, the emulsion is in the form of a cream.

In an embodiment, the compositions of the present disclosure are in the form of a gel cream.

Methods

Another aspect of the invention pertains to methods of using the hair cosmetic compositions described herein. The methods generally comprise applying any of the hair cosmetic compositions described to hair. The hair cosmetic compositions may be useful in a variety of settings, and either for chemically treated or untreated hair. Use on treated hair can include chemically relaxed/straightened hair or chemically dyed or bleached or lightened/highlighted hair. Use on hair may include as part of a shampoo, part of a conditioner or as a conditioner, as a pre-treatment, or after cleansing or conditioning or washing the hair as a leave-on treatment for styling/shaping the hair or caring for curly hair or as a leave-on or rinse-off mask treatment.

Methods of treating hair according to the disclosure may include applying a hair cosmetic composition of the instant disclosure to the hair (wet, damp, or dry hair), allowing the hair treatment to remain on the hair for a sufficient amount of time, and rinsing the hair cosmetic composition from the hair or allowing the hair treatment to be left on the hair as a leave-on product. The hair cosmetic composition may be applied to the hair before, during, or after other hair cosmetic compositions (e.g., a shampoo, a conditioner, a mask, a cream, a lotion, a gel, etc.).

Other methods of treating hair according to the disclosure involve a wash and go/braiding technique. Typically, the hair type on which this method is used is curly hair.

Other methods of treating hair according to the disclosure involve a twist out technique. Typically, the hair type on which this method is used is curly hair.

The hair cosmetic composition may be allowed to remain on the hair for a period of time, for example from about a few seconds (1, 3, 5, or 10 seconds) to about 10, 20, or 30 minutes, or longer such as up to about one hour or up to about two hours or up to about three hours or up to about four hours or up to about five hours or up to about six hours or up to about seven hours or up to about eight hours or up to about 12 hours.

The hair cosmetic compositions may be useful for treating chemically treated hair.

Described above is the individual application of a hair cosmetic composition or the combined or layered application of a hair cosmetic composition with another composition. In some cases, a hair cosmetic composition is individually applied to the hair and also combined or layered with another composition that is also applied to the hair.

Kits

The hair cosmetic compositions of the instant disclosure may be incorporated into a kit. For example, the kits may include at least one hair cosmetic composition according to the instant disclosure. The kits may also include one or more hair cosmetic compositions (according the instant disclosure), a shampoo and/or a conditioner and/or a mask.

Implementation of the present disclosure is provided by way of the following examples. The examples serve to illustrate the technology without being limiting in nature.

EXAMPLES

The following Examples are intended to be non-restrictive and explanatory only. The ingredient amounts in the compositions/formulas described below are expressed in % by weight, based on the total weight of the composition.

Several formulas were produced having the ingredients as listed in the tables below. The balance of all formulas was water.

Example I: Compositions

TABLE 1

| Ingredient Type | INCI NAME | Formula A Gel Cream | Formula B Gel Cream | Formula C Emulsion Cream | Formula D Gel Cream |
|---|---|---|---|---|---|
| Gums | HYDROXYPROPYL GUAR | 0.6 | 1 | 1.3 | 0.3 |
| | SCLEROTIUM GUM | — | — | 0.3 | — |
| | XANTHAN GUM | 0.6 | 0.6 | — | 0.3 |
| Fatty alcohol | CETEARYL ALCOHOL | 2-4 | 2-4 | 2-4 | 2-4 |
| | CETEARYL GLUCOSIDE | — | — | 0.6 | — |
| Glyceryl ester | GLYCERYL STEARATE | 3 | 3 | — | 2.5 |
| | BIS-DIGLYCERYL POLYACYLADIPATE-2 | — | — | 1 | — |
| Other esters | ISOPROPYL MYRISTATE AND/OR CETYL ESTERS | 2.1 | 2.1 | 2 | 1.4 |
| Plant- or vegetable-based fatty compound | *BUTYROSPERMUM PARKII* (SHEA) BUTTER | 1 | 0.5 | 0.5 | 0.01 |
| | *COCOS NUCIFERA* (COCONUT) OIL | 1 | 1 | 0.5 | 0.01 |
| | *RICINUS COMMUNIS* (CASTOR) SEED OIL | — | 2 | — | — |
| Additives | FILLERS AND/OR SUGARS AND/OR VITAMINS AND/OR PLANT EXTRACTS | <6 | <6 | <6 | <6 |
| Organic Solvents | GLYCERIN AND/OR CAPRYLYL GLYCOL | <5 | <5 | <5 | <5 |
| Preservative, pH adjusters, fragrance | SODIUM BENZOATE | <2 | <2 | <2 | <2 |
| | WATER | QS 100 | QS 100 | QS 100 | QS 100 |

In order to obtain a gel cream, the invention employs the combination of hydroxypropyl guar as a first gum, xanthan gum as a second gum, and glyceryl stearate as the glyceryl ester.

In order to obtain an emulsion cream, the invention employs *sclerotium* gum as the second gum, bis-diglyceryl polyacyladipate as the glyceryl ester, and alkyl polyglucoside, in addition to the fatty alcohol.

Process of Making the Invention Compositions:

The gel cream formulas A, B, and D were prepared according to the following process:

An all in one process was used to formulate these formulas. For each formula, a batch is initiated with 22% Water and the gums in a main kettle in order for the gums to be fully hydrated at 25C. The batch is heated at 65-70° C. to which preservative(s), ester(s), fatty alcohol(s), vegetable oil(s)/vegetable-based components, and fragrance are added. The remaining amount of water needed is added in the end to cool the batch to room temperature.

The emulsion cream formula C was prepared according to the following process:

For each formula, a batch is initiated with 44% Water and the gums in a amin kettle in order for the gums to be fully hydrated at 25 C. The batch is heated at 55-60° C. to which preservative(s) are added. A side kettle is prepared by heating ester(s), fatty alcohols, and vegetable based fatty components. The mixture in the side kettle is then added to the main kettle followed by the addition of fragrance. The remaining water needed is added in the end to cool batch to room temperature.

Example II Testing the Contributions of the Various Ingredients in the Invention Compositions While developing the invention compositions, the inventors discovered associations of ingredients that were lightweight (not a heavy coating) on hair, specifically curly hair, but still gave a lengthening (or elongation or stretching) effect to the curls.

Hydroxypropyl Guar was found to provide slip, smoothness, and definition to curls. However, the inventors found that formulas with only one gum, hydroxypropyl guar gum, did not result in stable formula and did not result in good curl elongation or curl stretching effects. Other gums such as carrageenan gum and cellulose gum were combined with hydroxypropyl guar. However, when carrageenan gum was combined with hydroxypropyl guar, the hair felt more straw-like & stiff and did not have enough slip to the hair. When cellulose gum was combined with hydroxypropyl guar, the hair felt heavily coated and did not provide hold/control to the curls. Dehydroxyxanthan gum and acacia gum were also explored. However, the use of these gums either did not provide hold/control to the curls or the desired formulation rheology/viscosity. The rheology needed to be a gel-like or cream-like consistency in order to support the fatty alcohol stabilizing system for stability purposes, but the use of acacia gum, for instance, gave a more flowable rheology.

On the other hand, two other gums, xanthan gum and *sclerotium* gum, each in combination with hydroxypropyl guar, unexpectedly provided the desired attributes, including curl elongation or stretching. It was surprisingly found that combining *sclerotium* gum with hydroxypropyl guar resulted in a composition that provided light and bounce movement to the curls without comprising other benefits. It was also surprisingly found that combining hydroxypropyl guar and xanthan gum displayed a "stretching effect" on the curls while still maintaining other styling benefits such as frizz-control and non-stiff feel.

For the gel cream, the use of glyceryl stearate was found to provide smoothness and conditioning to the hair without compromising curl definition as opposed to the use of tribehenin esters which did not result in sufficient curl definition.

For the emulsion cream, the use of Bis-diglyceryl Polyacyladipate-2 provided a light weight feel to the hair. Another glyceryl ester, glyceryl oleate was found to be create a heavier coating on hair.

The use of *Ricinus communis* (Castor) Seed Oil resulted in providing hydration and curl elongation without making the hair too greasy. The use of other oils, such as camelina and linseed, were found to create a heavy coating on hair.

For the emulsion cream invention formula, it was found that using a fatty alcohol alone did not contribute the level of conditioning that the fatty alcohol/alkylpolyglucoside combination displayed. Also, the fatty alcohol alone did not provide the required formula stability to the emulsion cream.

The use of *Cocos nucifera* (Coconut) Oil which has a high content of saturated fatty acids helped benefits such as penetration, frizz control, and a smooth after feel. The use of *Butyrospermum parkii* (Shea) Butter helped provide lubrication and sheen to the hair. It left the hair feeling and looking non-greasy.

The use of Isopropyl Myristate (IPM) was found to provide hydration and moisturization to the hair.

For the gel cream, the combination of the fatty alcohol, castor seed oil, and cetyl esters stabilized the gel cream.

The use of other oils such as olive oil, rapeseed oil, avocado oil, sunflower oil and apricot oil were explored, but they did not provide sufficient control to frizz on curly hair or were too heavy on hair and did not provide appreciable shine or did not provide moisturization to the hair.

In combining the oils, fatty compounds, and gums described above, the inventors surprisingly discovered a formula that gave all the desired benefits, including curl elongation or stretching, while still leaving a clean feel and light weight feel on the hair, i.e., it did not leave the hair feeling greasy or dirty.

Stability testing of the formulas were conducted in 25° C. & 45° C. for 8 weeks and 60° C. for 1 week to ensure that the emulsion is stable within these cycles. The formula is not stable when stability failed before completion of the 8 week and/or 1 week study at any of the designated temperatures.

Example III Testing Various Combinations of Gums

The formulas/compositions of the invention can be considered to be a hybrid technology that relies on a combination of specific gums, esters and fatty compounds to achieve the most commonly desired attributes amongst people with curly hair.

Table 2 below depicts the evaluator assessments of the hair of mannequin heads treated with formulas containing various combinations of gums. Formula C in Table 1 was used as the "base formula" from which several formulas containing different gum combinations were prepared for the test.

TABLE 2

| | | Gum Combination Analysis | | | | | | | |
|---|---|---|---|---|---|---|---|---|---|
| Combination | Ratio of RMs (2:1) | Curl Definition | Soft Feel | Crunch | Hold | Elongation | Frizz Control | Slip on Hair | Moisture |
| I | Hyroxypropyl Guar/Xanthan Gum | ✓ | ✓ | ✓ | ✓ | ✓ | ✓ | ✓ | ✓ |
| II | Hyroxypropyl Guar/Acacia Gum | — | ✓ | ✓ | X | X | — | ✓ | — |
| III | Hyroxypropyl Guar/Sclerotium Gum | ✓ | ✓ | ✓ | ✓ | ✓ | ✓ | ✓ | ✓ |
| IV | Hyroxypropyl Guar/Hydroxethyl Cellulose | — | — | — | — | X | — | ✓ | ✓ |
| V | Hyroxypropyl Guar/Carrageenan | ✓ | X | X | ✓ | X | — | — | — |
| VI | Hyroxypropyl Guar/Pectin | ✓ | ✓ | ✓ | — | X | ✓ | ✓ | ✓ |
| VII | Hyroxypropyl Guar/Dehydroxyxanthan Gum | ✓ | ✓ | — | — | ✓ | — | ✓ | ✓ |

Table 2 Legend
Positive (Desirable Results) ✓
Negative X
Neutral results —

The results in Table 2 above show that all attributes that were assessed were observed on the hair treated with the formulas containing Combination I (hydroxypropyl guar and xanthan gum in a weight ratio of 2:1) or Combination II (hydroxypropyl guar and *sclerotium* gum in a weight ratio of 2:1). The hair treated with the other combinations did not impart all the attributes. In particular, only Combinations I and II, and one other, Combination VII, imparted curl elongation effects. Also, only Combinations I and II, and one other, Combination VI, imparted frizz control effects.

Example IV Testing Against a Commercial Product

The curl elongation or curl stretching effect imparted by Formula C was compared to that of a commercial product (Comparative Formula X) that claims for curl stretching. Hair swatches of very curly hair were treated with each test formula. The results are depicted in FIG. 1.

Table 3 Commercial product (Comparative Formula X) breakdown Water, Cetearyl Alcohol, *Linum usitatissimum* (Linseed) Seed Oil, *Butyrospermum parkii* (Shea) Butter, Glycerin (Vegetable), Stearyl Alcohol, Behentrimonium Methosulfate, Cetyl Alcohol, *Prunus amygdalus dulcis* (Sweet Almond) Oil, Behentrimonium Chloride, Fragrance (Essential Oil Blend), Panthenol, *Elaeis guineensis* (Palm) Oil, Hydrolyzed Soy Protein, *Theobroma cacao* (Cocoa)

Seed Butter, *Persea gratissima* (Avocado) Oil, Hydrogenated Vegetable Oil, Vitamin(s), cationic surfactant(s), plant extracts, preservatives.

Curly hair swatches were each treated with the invention Formula C and with Comparative Formula X. FIG. 1 shows the swatches after the treatment—swatch on the left was treated with Formula C and the swatch on the right was treated with the Comparative Formula X.

As seen from FIG. 1, the treatment of hair with inventive formula C resulted in significantly better curl elongation or curl stretching effect, curl definition and frizz/volume control as compared to the treatment with Comparative Formula X.

From these results we can conclude that the combination of ingredients in the inventive formula has the curl elongation properties sought for curly hair.

Example V Testing the Oiliness of Hair

In order to demonstrate that the invention formula leaves a clean feel to hair (not a greasy/oily feel), oil absorbing sheets were wiped on hair treated with either the invention formula or the commercial product, Comparative Formula X, to test how much oily residue was left on the hair.

Oil absorbing sheets wiped on hair swatches treated with Comparative Formula X and with the invention Formula C. The results are demonstrated in FIG. 2—the sheet on the left was treated with Comparative Formula X and the sheet on the right was treated with the Invention Formula C.

Figure 2:
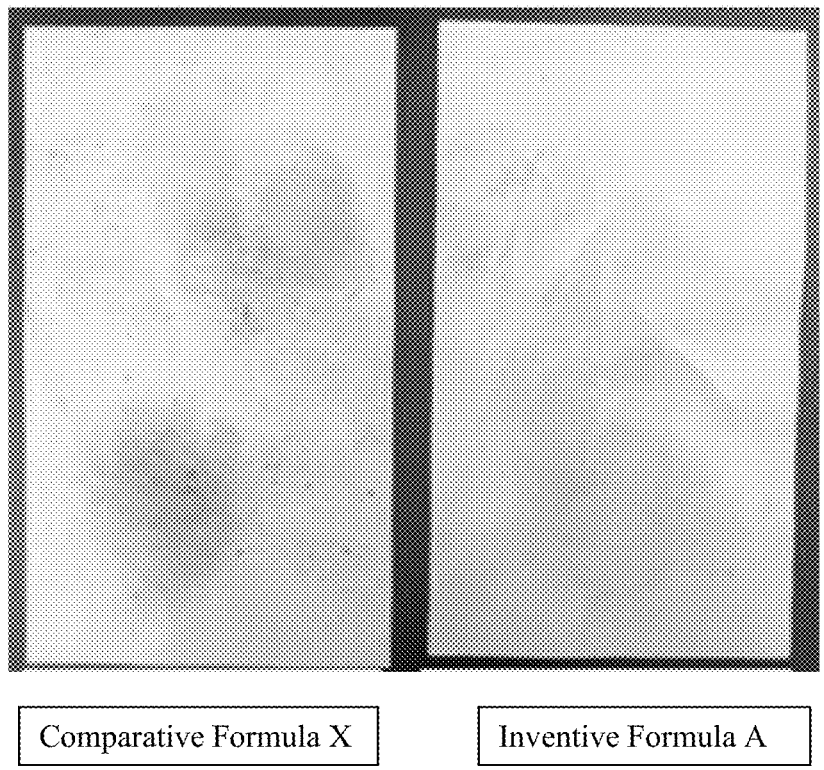
FIG. 2 includes pictures of oil absorbing sheets that have wiped on hair swatches treated with a comparative formula (sheet on the left) and with the invention formula (sheet on the right).

As seen from FIG. 2, the treatment of hair with inventive formula C resulted in significantly less oiliness on hair as compared to the treatment with Comparative Formula X.

From these results we can conclude that the combination of ingredients in the inventive formula provides the right amount of oil sought for curly hair which is related to leaving the hair feeling clean and light weight and not oily or greasy.

In summary, the examples above show that the inventors surprisingly discovered a combination of ingredients that resulted in compositions in the form of gel creams or emulsion creams that not only provided styling and shaping benefits to hair but when used on curly hair, provided curl definition, good hold/control to the hair shape, good frizz and volume control, and curl elongation or stretching, while still being light weight on hair and leaving a clean feel on hair (not heavy coating and not greasy/oily).

The foregoing description illustrates and describes the invention. The disclosure shows and describes only the preferred embodiments but it should be understood that the invention is capable to use in various other combinations, modifications, and environments and is capable of changes or modifications within the scope of the inventive concepts as expressed herein, commensurate with the above teachings and/or the skill or knowledge of the relevant art. The embodiments described herein above are further intended to explain best modes known by applicant and to enable others skilled in the art to utilize the disclosure in such, or other, embodiments and with the various modifications required by the particular applications or uses thereof. Accordingly, the description is not intended to limit the invention to the form disclosed herein.

As used herein, the terms "comprising," "having," and "including" (or "comprise," "have," and "include") are used in their open, non-limiting sense. The phrase "consisting essentially of" limits the scope of a claim to the specified materials or steps and those that do not materially affect the basic and novel characteristics of the claimed invention.

The terms "a," "an," and "the" are understood to encompass the plural as well as the singular.

Thus, the term "a mixture thereof" also relates to "mixtures thereof." Throughout the disclosure, if the term "a mixture thereof" is used, following a list of elements as shown in the following example where letters A-F represent the elements: "one or more elements selected from the group consisting of A, B, C, D, E, F, or mixtures thereof." The term, "a mixture thereof" does not require that the mixture include all of A, B, C, D, E, and F (although all of A, B, C, D, E, and F may be included). Rather, it indicates that a mixture of any two or more of A, B, C, D, E, and F can be included. In other words, it is equivalent to the phrase "one or more elements selected from the group consisting of A, B, C, D, E, F, and a mixture of any two or more of A, B, C, D, E, and F."

Likewise, the term "a salt thereof" also relates to "salts thereof." Thus, where the disclosure refers to "an element selected from the group consisting of A, B, C, D, E, F, a salt thereof, or mixtures thereof," it indicates that that one or more of A, B, C, D, and F may be included, one or more of a salt of A, a salt of B, a salt of C, a salt of D, a salt of E, and a salt of F may be included, or a mixture of any two of A, B, C, D, E, F, a salt of A, a salt of B, a salt of C, a salt of D, a salt of E, and a salt of F may be included.

The salts referred to throughout the disclosure may include salts having a counter-ion such as an alkali metal, alkaline earth metal, or ammonium counterion. This list of counterions, however, is non-limiting.

The expression "one or more" means "at least one" and thus includes individual components as well as mixtures/combinations.

The term "plurality" means "more than one" or "two or more."

The term "lasting" or "long lasting" or "durable" as used herein means that the cosmetic attribute or effect was observed up to about 30 minutes or up to about one hour or up to about two hours, or up to about three hours or up to about four hours or up to about five hours or up to about six hours or up to about seven hours or up to about eight hours or up to about 12 hours from the time the composition of the present disclosure was applied to hair on the head of a person.

Some of the various categories of components identified for the hair-treatment compositions may overlap. In such cases where overlap may exist and the composition/product includes two overlapping components (or more than two overlapping components), an overlapping component does not represent more than one component. For example, a fatty acid may be defined as both a "fatty compound" and a "surfactant/emulsifier." If a particular composition/product includes both a fatty compound component and an emulsifier component, a single fatty acid can serve as only a fatty compound or a surfactant/emulsifier (a single fatty acid does not serve as both the fatty compound and the surfactant/emulsifier).

All percentages, parts and ratios herein are based upon the total weight of the compositions of the present invention, unless otherwise indicated.

All ranges and values disclosed herein are inclusive and combinable. For examples, any value or point described herein that falls within a range described herein can serve as a minimum or maximum value to derive a sub-range, etc. Furthermore, all ranges provided are meant to include every specific range within, and combination of sub-ranges between, the given ranges. Thus, a range from 1-5, includes specifically points 1, 2, 3, 4 and 5, as well as sub-ranges such as 2-5, 3-5, 2-3, 2-4, 1-4, etc.; and points of 1, 2, 3, 4, and 5 includes ranges and sub-ranges of 1-5, 2-5, 3-5, 2-3, 2-4, 1-4, etc.

Other than in the operating examples, or where otherwise indicated, all numbers expressing quantities of ingredients and/or reaction conditions are understood to be modified by "about," whether or not expressly stated. Additionally, all numbers are intended to represent exact figures as additional embodiments, whether or not modified by "about." For example, "an amount of about 1%" includes an amount of exactly 1%. As a further example, "an amount of 1%" includes an amount of about 1%. The term "about" is generally understood to encompass a range of +/−10% from the stated number, and is intended to cover amounts of +/−1%, 2%, 3%, 4%, 5%, 6%, 7%, 8%, 9%, and 10%.

The term "surfactants" includes salts of the surfactants even if not explicitly stated. In other words, whenever the disclosure refers to a surfactant, it is intended that salts of the surfactant are also encompassed to the extent such salts exist, even though the specification may not specifically refer to a salt (or may not refer to a salt in every instance throughout the disclosure), for example, by using language such as "a salt thereof" or "salts thereof." Sodium and potassium are common cations that form salts with surfactants. However, additional cations such as ammonium ions, or alkanolammonium ions such as monoethanolammonium or triethanolammonium ions, may also form salts of surfactants.

The term "substantially free" or "essentially free" as used herein means the specific material may be present in small amounts that do not materially affect the basic and novel characteristics of the claimed invention. For instance, there may be less than 2% by weight of a specific material added to a composition, based on the total weight of the compositions (provided that an amount of less than 2% by weight does not materially affect the basic and novel characteristics of the claimed invention. Similarly, the compositions may include less than 2 wt %, less than 1.5 wt %, less than 1 wt %, less than 0.5 wt %, less than 0.1 wt %, less than 0.05 wt %, or less than 0.01 wt %, or none of the specified material. Furthermore, all components that are positively set forth in the instant disclosure may be negatively excluded from the claims, e.g., a claimed composition may be "free," "essentially free" (or "substantially free") of one or more components that are positively set forth in the instant disclosure.

The term "substantially free" or "essentially free" as used herein may also mean that the specific material is not added to the composition but may still be present in a raw material that is included in the composition.

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

The invention claimed is:

1. A hair cosmetic composition comprising:
 (a) about 0.01 to about 3 wt. % of hydroxypropyl guar;
 (b) about 0.01 to about 3 wt. % of a second gum selected from xanthan gum, *sclerotium* gum, and a mixture thereof;
 (c) 1.5 to about 8 wt. % of at least one fatty alcohol;
 (d) about 0.6 to about 4.5 wt % of at least one glyceryl ester selected from glyceryl stearate, bis-diglyceryl polyacyladipate, and a mixture thereof;
 (e) about 0.5 to about 3 wt % of at least one ester that is not a glyceryl ester;
 (f) a plant- or vegetable-based fatty component comprising coconut oil and shea butter; and
 (g) about 60 to about 90 wt. % of water;
  all weights being based on the hair cosmetic composition total weight.

2. The hair cosmetic composition of claim 1, wherein the second gum is xanthan gum.

3. The hair cosmetic composition of claim 1, wherein the second gum is *sclerotium* gum.

4. The hair cosmetic composition of claim 1, wherein the at least one fatty alcohol is selected from cetyl alcohol, stearyl alcohol, cetearyl alcohol, behenyl alcohol, lauryl alcohol; myristic or myristyl alcohol, arachidyl alcohol, lignoceryl alcohol; ceryl alcohol; montanyl alcohol; myricylic alcohol, decyl alcohol, undecyl alcohol, and mixtures thereof.

5. The hair cosmetic composition of claim 1, wherein the at least one fatty alcohol is present in an amount of 1.5% to about 6%, based on the hair cosmetic composition total weight.

6. The hair cosmetic composition of claim 1, wherein the at least one glyceryl ester is glyceryl stearate.

7. The hair cosmetic composition of claim 1, wherein the at least one glyceryl ester is bis-diglyceryl polyacyladipate.

8. The hair cosmetic composition of claim 1, wherein the at least one ester that is not a glyceryl ester is selected from isopropyl esters, cetyl esters, or mixtures thereof.

9. The hair cosmetic composition of claim 1, wherein the at least one ester that is not a glyceryl ester is isopropyl myristate, isopropyl laurate, isopropyl oleate, isopropyl palmitate, isopropyl stearate, or mixtures thereof.

10. The hair cosmetic composition of claim 1, wherein the plant- or vegetable-based fatty component is present in an amount of about 0.01 to about 5 wt. %, based on the hair cosmetic composition total weight.

11. The hair cosmetic composition of claim 1, wherein the plant- or vegetable-based fatty component further comprises castor seed oil.

12. The hair cosmetic composition of claim 1, further comprising at least one alkylpolyglucoside, wherein the at least one alkylpolyglucoside is present in an amount of about 0.1 to about 8 wt. %, based on the hair cosmetic composition total weight.

13. The hair cosmetic composition of claim 12, wherein the at least one alkylpolyglucoside is selected from Arachidyl Glucoside, C12-20 Alkyl Glucoside, Caprylyl/Capryl Glucoside, Cetearyl Glucoside, Coco-Glucoside, Lauryl Glucoside, Decyl Glucoside, or mixtures thereof.

14. The hair cosmetic composition of claim 1, wherein:
 the second gum is xanthan gum,
 the at least one glyceryl ester is glyceryl stearate, the at least one ester that is not a glyceryl ester comprises isopropyl esters, cetyl esters, or a mixture thereof.

15. The hair cosmetic composition of claim 14, wherein the composition is in the form of a gel cream.

16. The hair cosmetic composition of claim 1, wherein:
 the second gum is *sclerotium* gum,
 the at least one glyceryl ester is bis-diglyceryl polyacyladipate, and
 the at least one ester that is not a glyceryl ester is isopropyl myristate, and wherein the composition further comprises at least one alkylpolyglucoside.

17. The hair cosmetic composition of claim 16, wherein the composition is in the form of an emulsion cream.

18. A hair cosmetic composition comprising:
(a) about 0.1 to about 3 wt. % of hydroxypropyl guar;
(b) about 0.01 to about 3 wt. % of xanthan gum, *sclerotium* gum, or a mixture thereof;
(c) about 2 to about 6 wt % of cetearyl alcohol;
(d) about 0.6 to about 4.5 wt % of glyceryl stearate, bis-diglyceryl polyacyladipate, or a mixture thereof;
(e) about 0.5 to about 3 wt % of isopropyl myristate, cetyl esters, or a mixture thereof;
(f) optionally, about 0.1 to about 8 wt. % of cetearyl glucoside;
(g) about 0.01 to about 5 wt. % of a combination of coconut oil and shea butter, and optionally castor seed oil;
(h) about 0.1 to about 10 wt. % of an organic solvent selected from $C_{1-6}$ alcohols, polyhydric alcohols, glycols, and mixtures thereof;
(i) less than 6 wt. % of fillers, sugars, vitamins, plant extracts, and mixtures thereof;
(j) less than 2 wt. % of preservatives, pH adjusters, fragrances, and mixtures thereof; and
(k) about 60 to about 90 wt. % of water;
all weights being based on the hair cosmetic composition total weight.

19. A hair cosmetic composition consisting of:
(a) about 0.1 to about 3 wt. % of hydroxypropyl guar;
(b) about 0.01 to about 3 wt. % of xanthan gum, *sclerotium* gum, or a mixture thereof;
(c) about 2 to about 6 wt % of cetearyl alcohol;
(d) about 0.6 to about 4.5 wt % of glyceryl stearate, bis-diglyceryl polyacyladipate, or a mixture thereof;
(e) about 0.5 to about 3 wt % of isopropyl myristate, cetyl esters, or a mixture thereof;
(f) optionally, about 0.1 to about 8 wt. % of cetearyl glucoside;
(g) about 0.01 to about 5 wt. % of a combination of coconut oil and shea butter, and optionally castor seed oil;
(h) about 0.1 to about 10 wt. % of an organic solvent selected from $C_{1-6}$ alcohols, polyhydric alcohols, glycols, and mixtures thereof;
(i) less than 6 wt. % of fillers, sugars, vitamins, plant extracts, or mixtures thereof;
(j) less than 2 wt. % of preservatives, pH adjusters, fragrances, or mixtures thereof; and
(k) about 60 to about 90 wt. % of water;
all weights being based on the hair cosmetic composition total weight.

20. A method for treating hair comprising applying a hair cosmetic composition of claim 1 to the hair.

* * * * *